United States Patent
Kim et al.

(10) Patent No.: US 10,047,196 B2
(45) Date of Patent: Aug. 14, 2018

(54) ORGANIC ZINC CATALYST, AND MANUFACTURING METHOD THEREOF AND MANUFACTURING METHOD OF POLYALKYLENE CARBONATE RESIN USING THE SAME (AS AMENDED)

(71) Applicant: LG CHEM, LTD., Seoul (KR)

(72) Inventors: Sung-Kyoung Kim, Daejeon (KR); Seung Young Park, Daejeon (KR); Hyun Ju Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/034,696

(22) PCT Filed: Nov. 18, 2014

(86) PCT No.: PCT/KR2014/011081
§ 371 (c)(1),
(2) Date: May 5, 2016

(87) PCT Pub. No.: WO2015/072815
PCT Pub. Date: May 21, 2015

(65) Prior Publication Data
US 2016/0272760 A1    Sep. 22, 2016

(30) Foreign Application Priority Data

Nov. 18, 2013 (KR) .......................... 10-2013-0139987
Nov. 18, 2014 (KR) .......................... 10-2014-0160747

(51) Int. Cl.
*C08G 64/34* (2006.01)
*B01J 31/12* (2006.01)
(Continued)

(52) U.S. Cl.
CPC .............. *C08G 64/34* (2013.01); *B01J 31/12* (2013.01); *B01J 31/2239* (2013.01); *C07F 3/06* (2013.01);
(Continued)

(58) Field of Classification Search
CPC .................................................... C08G 64/34
(Continued)

(56) References Cited

U.S. PATENT DOCUMENTS

| 4,943,677 A | 7/1990 | Rokicki |
| 5,026,676 A | 6/1991 | Motika et al. |

(Continued)

FOREIGN PATENT DOCUMENTS

| DE | 19737547 A1 | 3/1999 |
| EP | 1532192 B1 | 8/2008 |

(Continued)

OTHER PUBLICATIONS

Jong-Seong Kim et al.: "X-ray absorption and NMR spectroscopic investigations of zinc glutarates prepared from various zinc sources and their catalytic activities in the copolymerization of carbon dioxide and propylene oxide", Journal of Catalysis 218 (2003) pp. 209-219.

(Continued)

*Primary Examiner* — Duc Truong
(74) *Attorney, Agent, or Firm* — Dentons US LLP

(57) ABSTRACT

The present disclosure relates to an organic zinc catalyst suppressing agglomeration among catalyst particles during a manufacturing method to have more uniform and finer particle size, thereby showing a more improved activity in a polymerization process for manufacturing a polyalkylene carbonate resin, a manufacturing method thereof, and a manufacturing method of a polyalkylene carbonate resin using the same, wherein the organic zinc catalyst is a zinc (Continued)

dicarboxylate-based organic zinc catalyst used for a reaction in which a polyalkylene carbonate resin is manufactured from carbon dioxide and epoxide and includes a monocarboxylic acid-derived moiety having a C3-C15 aliphatic hydrocarbon group (provided that at least one oxygen or carbonyl group is included or not included in the aliphatic hydrocarbon group) that is bonded to an end of at least one side of the zinc dicarboxylate-based organic zinc catalyst.

12 Claims, 1 Drawing Sheet

(51) Int. Cl.
| | | |
|---|---|---|
| *C08K 5/56* | (2006.01) | |
| *B01J 31/22* | (2006.01) | |
| *C07F 3/06* | (2006.01) | |
| *C08G 64/02* | (2006.01) | |

(52) U.S. Cl.
CPC .......... *C08G 64/0208* (2013.01); *C08K 5/56* (2013.01); *B01J 2231/14* (2013.01); *B01J 2531/26* (2013.01)

(58) Field of Classification Search
USPC ........................................ 528/414
See application file for complete search history.

(56) References Cited

U.S. PATENT DOCUMENTS

| | | |
|---|---|---|
| 2003/0134740 A1 | 7/2003 | Meng et al. |
| 2004/0214718 A1 | 10/2004 | Meng et al. |
| 2009/0240025 A1 | 9/2009 | Fujimoto et al. |
| 2011/0218320 A1 | 9/2011 | Steinke et al. |
| 2011/0218321 A1 | 9/2011 | Steinke et al. |
| 2012/0123066 A1 | 5/2012 | Fujimoto et al. |
| 2012/0184563 A1 | 7/2012 | Hanma |

FOREIGN PATENT DOCUMENTS

| | | | |
|---|---|---|---|
| EP | 2017297 | * | 1/2009 |
| EP | 2433976 | A1 | 3/2012 |
| JP | 2571269 | B2 | 1/1997 |
| JP | 2693584 | B2 | 9/1997 |
| JP | 2732475 | B2 | 12/1997 |
| JP | 2006-257374 | A | 9/2006 |
| KR | 2003-0097237 | A | 12/2003 |
| KR | 10-2009-0025219 | A | 3/2009 |
| KR | 10-2012-0023820 | A | 3/2012 |
| WO | 2010146872 | A1 | 12/2010 |
| WO | 2011/004730 | A1 | 1/2011 |

OTHER PUBLICATIONS

Jong-Seung Kim et al.: "Hydrothermal Synthesis of Single-Crystalline Zinc Glutarate and Its Structural Determination", Chem Mater. 2004, 16, pp. 2981-2983.

ICSC 0806—Propionic Acid, IPCS in Chem, Peer-Review Status: Oct. 9, 1997 Validated at http://www.nihs.go.jp/ICSC/icssj-c/icss0806c.html, (http://www.inchem.org/documents/icsc/icsc/eics0806.htm).

* cited by examiner

[FIG. 1]
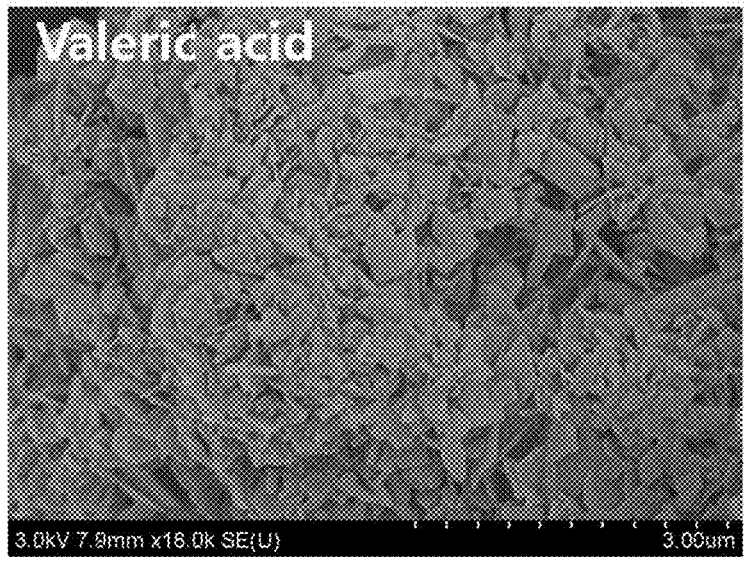
[FIG. 2]
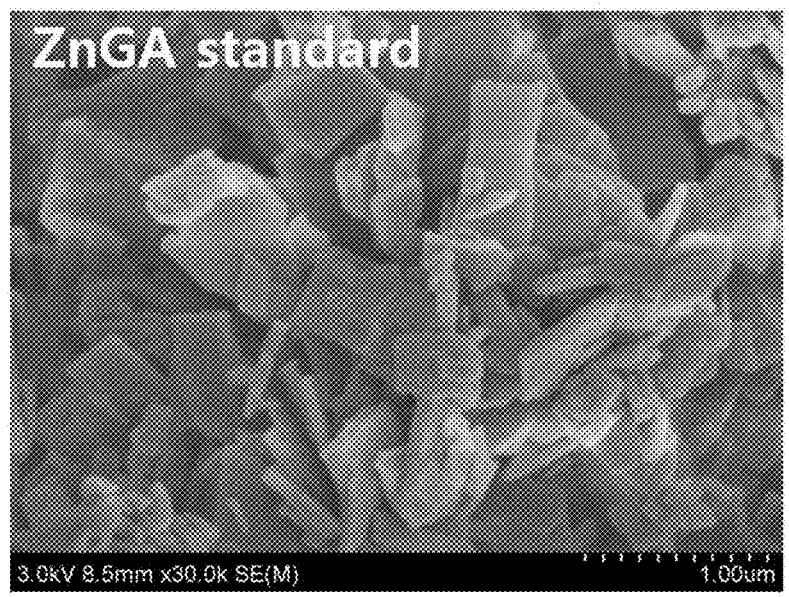

ORGANIC ZINC CATALYST, AND MANUFACTURING METHOD THEREOF AND MANUFACTURING METHOD OF POLYALKYLENE CARBONATE RESIN USING THE SAME (AS AMENDED)

This application is a National Stage Entry of International Application No. PCT/KR2014/011081, filed on Nov. 18, 2014, and claims the benefit of and priority to Korean Application No. 10-2013-0139987, filed on Nov. 18, 2013, and Korean Application No. 10-2014-0160747, filed on Nov. 18, 2014, all of which are incorporated herein by reference in their entirety for all purposes as if fully set forth herein.

TECHNICAL FIELD

The present invention relates to an organic zinc catalyst suppressing agglomeration among catalyst particles during a manufacturing process to have more uniform and finer particle size, thereby showing a more improved activity in a polymerization process for manufacturing a polyalkylene carbonate resin, a manufacturing method thereof, and a manufacturing method of a polyalkylene carbonate resin using the same.

BACKGROUND

Since the industrial revolution, modern society has been built by consuming a large amount of fossil fuels, but on the other hand, carbon dioxide concentration in the atmosphere is increased, and further, this increase is more accelerated by environmental destruction such as disforestation, etc.

Global warming is caused by an increase of greenhouse gases such as carbon dioxide, freon, and methane in the atmosphere, such that it is significantly important to reduce the atmospheric concentration of carbon dioxide highly contributing to global warming, and several studies into emission regulation, immobilization, etc., have been conducted on a global scale.

Among the studies, a copolymerization reaction of carbon dioxide and epoxide developed by Inoue, et al., is expected as a reaction for solving the problems of global warming, and has been actively researched in view of immobilization of chemical carbon dioxide and in view of the use of carbon dioxide as a carbon resource.

Particularly, a polyalkylene carbonate resin obtained by the polymerization of carbon dioxide and epoxide has recently received significant attention as a kind of biodegradable resins.

Various catalysts for manufacturing the polyalkylene carbonate resin have been researched and suggested for a long time, and as representative examples thereof, zinc dicarboxylate-based catalysts such as a zinc glutarate catalyst, etc., in which zinc and dicarboxylic acid are combined to each other have been known.

Meanwhile, the zinc dicarboxylate-based catalyst, as a representative example, a zinc glutarate catalyst is formed by reacting a zinc precursor with a dicarboxylic acid such as a glutaric acid, etc., and has a shape of fine crystalline particle.

However, since there are a number of cases in which agglomeration among catalyst particles occurs in a manufacturing process of the catalyst, a case in which the catalyst has a relatively large particle size and a non-uniform particle shape has frequently occurred.

Due to the large and non-uniform particle size, etc., there is a drawback in which if a polymerization process for manufacturing a polyalkylene carbonate resin by using a zinc dicarboxylate-based catalyst is performed, a sufficient contact area between reactants and the catalyst is not secured, such that a polymerization activity is not sufficiently expressed.

Due to the drawback, development of a catalyst-relevant technology which is possible to provide a catalyst capable of suppressing agglomeration among the catalyst particles during the manufacturing process of the catalyst and showing a more improved activity, etc., has been continuously demanded.

SUMMARY OF THE INVENTION

The present invention provides an organic zinc catalyst and a manufacturing method thereof having advantages of suppressing agglomeration among catalyst particles during a manufacturing process to have a more uniform and finer particle size, thereby showing a more improved activity in a polymerization process for manufacturing a polyalkylene carbonate resin.

In addition, the present invention provides a manufacturing method of a polyalkylene carbonate resin using the organic zinc catalyst.

An exemplary embodiment of the present invention provides an organic zinc catalyst which is a zinc dicarboxylate-based organic zinc catalyst used for a reaction in which a polyalkylene carbonate resin is manufactured from carbon dioxide and epoxide, the organic zinc catalyst including a monocarboxylic acid-derived moiety having a C3-C15 aliphatic hydrocarbon group (provided that at least one oxygen or carbonyl group may be included or may not be included in the aliphatic hydrocarbon group) that is bonded to an end of at least one side of the zinc dicarboxylate-based organic zinc catalyst.

Another embodiment of the present invention provides a manufacturing method of the organic zinc catalyst as described above including: reacting a zinc precursor, a dicarboxylic acid, and a monocarboxylic acid having a C3-C15 aliphatic hydrocarbon group (provided that at least one oxygen or carbonyl group may be included or may not be included in the aliphatic hydrocarbon group).

Yet another embodiment of the present invention provides a manufacturing method of a polyalkylene carbonate resin including: polymerizing epoxide and a monomer including carbon dioxide in the presence of the organic zinc catalyst as described above.

Hereinafter, the organic zinc catalyst, the manufacturing method thereof, and the manufacturing method of the polyalkylene carbonate resin using the same, etc., according to exemplary embodiments of the present invention will be described in detail.

According to an exemplary embodiment of the present invention, there is provided an organic zinc catalyst which is a zinc dicarboxylate-based organic zinc catalyst used for a reaction in which a polyalkylene carbonate resin is manufactured from carbon dioxide and epoxide, the organic zinc catalyst including a monocarboxylic acid-derived moiety having a C3-C15 aliphatic hydrocarbon group (provided that at least one oxygen or carbonyl group may be included or may not be included in the aliphatic hydrocarbon group) that is bonded to an end of at least one side of the zinc dicarboxylate-based organic zinc catalyst.

From a structure of a zinc dicarboxylate-based organic zinc catalyst that is previously known in the art, the organic zinc catalyst according to an exemplary embodiment of the present invention has a structure in which the monocarboxylic acid-derived moiety having a C3-C15 aliphatic hydrocarbon group (e.g., a moiety having a structure of "(C3-C15 aliphatic hydrocarbon group)-(C=O)—O—") is bonded to an end of at least one side of the structure of the previously known zinc dicarboxylate-based organic zinc catalyst, thereby having an end-capping structure with the monocarboxylic acid-derived moiety.

Due to the end-capping structure, particularly, a structural characteristic which is end-capped with a structure containing an aliphatic hydrocarbon group having a relatively long chain length, end-capping structures having relative hydrophobicity may suppress agglomeration among the catalyst particles to each other.

Accordingly, the organic zinc catalyst may suppress agglomeration among the catalyst particles during the manufacturing process to have a more uniform and finer particle size.

As a result, it was confirmed that when the organic zinc catalyst according to an exemplary embodiment of the present invention was used to perform copolymerization of carbon dioxide and epoxide and manufacture the polyalkylene carbonate resin, contact areas among reaction materials for copolymerization and the organic zinc catalyst particles could be more increased, and a copolymerization activity could be significantly improved.

Therefore, the organic zinc catalyst according to an exemplary embodiment of the present invention may suppress agglomeration among the catalyst particles during the manufacturing process to have a more uniform and finer particle size and to show a more improved activity in the polymerization process for manufacturing the polyalkylene carbonate resin, such that the organic zinc catalyst may be very preferably used in the polymerization process.

The organic zinc catalyst may basically include the same chain structure as the zinc dicarboxylate-based catalyst that is previously known in the art.

That is, the organic zinc catalyst may have a structure in which zinc is bonded to dicarboxylate, for example, C3-C20 aliphatic dicarboxylate or C8-C40 aromatic dicarboxylate, provided that the monocarboxylate-derived moiety may be bonded to an end thereof.

For example, the organic zinc catalyst may have a chemical structure represented by General Formula 1 below:

[General Formula 1]

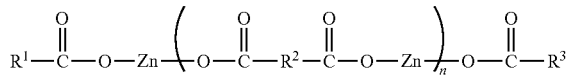

in General Formula 1 above, $R^1$ and $R^3$ each independently represent a C3-C15 aliphatic hydrocarbon group (provided that at least one oxygen or carbonyl group may be included or may not be included in the aliphatic hydrocarbon group) derived from a monocarboxylic acid, and $R^2$ represents C1-C20 aliphatic hydrocarbon group or C6-C40 aromatic hydrocarbon group derived from dicarboxylic acid or dicarboxylate.

In the structure of the organic zinc catalyst according to an exemplary embodiment of the present invention, the dicarboxylate may be any one selected from C3-C20 aliphatic dicarboxylates such as glutarate, malonate, succinate, adipate, etc., or C8-C40 aromatic dicarboxylates such as terephthalate, isophthalate, homophthalate, phenylglutarate, etc.

Meanwhile, in view of an activity, etc., of the organic zinc catalyst, it is preferred that the dicarboxylate is glutarate and the zinc dicarboxylate-based organic zinc catalyst is a zinc glutarate-based catalyst.

The dicarboxylate may be derived from dicarboxylic acid corresponding to the same, for example, C3-C20 aliphatic dicarboxylic acids such as glutaric acid, malonic acid, succinic acid, adipic acid, etc., or C8-C40 aromatic dicarboxylic acids such as terephthalic acid, isophthalic acid, homophthalic acid, phenylglutaric acid, etc., and may be formed by reaction of these dicarboxylic acids and zinc.

Further, the moiety that is bonded to and capped with an end of at least one side of the organic zinc catalyst may be derived from the monocarboxylic acid having C3-C15 or C4-C15 or C6-C15 aliphatic hydrocarbon group with or without at least one oxygen or carbonyl group. Representative examples of the monocarboxylic acid may include valeric acid, lauric acid, 3,5-dioxohexanoic acid, 3,5,7-trioxo-dodecanoic acid, keto acids such as acetoacetic acid, levulinic acid, etc.; or oxo carboxylic acids such as 4-oxo-4H-1-benzopyran-2-carboxylic acid, 5-hydroxy-4-oxo-4H-pyran-2-carboxylic acid, etc., and mixtures of two or more selected therefrom.

As the monocarboxylic acid-derived moiety is capped with the end of the organic zinc catalyst, agglomeration among the catalyst particles in the manufacturing process of the catalyst may be more effectively suppressed, such that the organic zinc catalyst having a more uniform and finer particle size and showing a more improved activity may be appropriately manufactured and provided.

Meanwhile, it is obvious that the organic zinc catalyst is capable of being end-capped with monocarboxylic acid-derived moiety through reaction with various monocarboxylic acids in addition to the above-described examples.

If an organic zinc catalyst that is end-capped with the monocarboxylic acid having an aliphatic hydrocarbon group with a carbon number of less than 3 (e.g., propionic acid, etc.) is used, it may be difficult for the aliphatic hydrocarbon group to show sufficient hydrophobicity and it may be difficult to suppress agglomeration among the catalyst particles.

Accordingly, it may be difficult to obtain the organic zinc catalyst having a fine and uniform particle size, and a polymerization activity of the organic zinc catalyst may not be sufficiently obtained.

Further, in the organic zinc catalyst according to an exemplary embodiment of the present invention, in order to more effectively suppress the agglomeration in the manufacturing method of the catalyst, it is more preferred that the monocarboxylic acid-derived moiety is capped with both ends of the zinc dicarboxylate-based organic zinc catalyst, and upon considering this, it is preferred that the monocarboxylic acid-derived moiety is bonded at about 0.1 to 0.5 molar ratio, or about 0.2 to 0.5 molar ratio, or about 0.2 to 0.4 molar ratio, relative to 1 mol of the dicarboxylate-derived moiety bonded to the organic zinc catalyst.

In addition, as the agglomeration among the catalyst particles may be suppressed in the manufacturing method thereof, the organic zinc catalyst according to the exemplary embodiment of the present invention may have a uniform particle shape in which an average particle size is about 0.2 to 0.9 μm, or about 0.3 to 0.8 μm, or about 0.5 to 0.7 μm and a particle size standard deviation is about 0.05 to 0.3 μm, or about 0.05 to 0.2 μm, or about 0.05 to 0.1 μm.

Accordingly, when the organic zinc catalyst is used as the catalyst at the time of manufacturing the polyalkylene carbonate resin by a copolymerization of carbon dioxide and epoxide, contact areas of catalyst particles and reaction materials may be more increased, thereby showing an improved activity.

Meanwhile, according to another exemplary embodiment of the present invention, there is provided a manufacturing method of the organic zinc catalyst according to the exemplary embodiment of the present invention.

The manufacturing method of the organic zinc catalyst may include, for example, reacting a zinc precursor, a dicarboxylic acid, and a monocarboxylic acid having a C3-C15 aliphatic hydrocarbon group (provided that at least one oxygen or carbonyl group may be included or may not be included in the aliphatic hydrocarbon group).

More specifically, in the manufacturing method, the reaction step may include reacting the zinc precursor with the dicarboxylic acid, and further reacting with the monocarboxylic acid.

According to the manufacturing method, the zinc precursor may be reacted with the dicarboxylic acid to manufacture the zinc dicarboxylate-based catalyst, and the monocarboxylic acid may be added thereto, such that agglomeration among additional catalyst particles may be suppressed while end-capping each catalyst, thereby finally manufacturing the organic zinc catalyst according to an exemplary embodiment of the present invention.

Accordingly, the organic zinc catalyst having a more uniform and finer particle size and showing an improved activity according to an exemplary embodiment of the present invention may be manufactured.

In the manufacturing process, as the zinc precursor, zinc salts such as zinc oxide, zinc hydroxide, zinc acetate (Zn ($O_2CCH_3$)$_2$), zinc nitrate ($Zn(NO_3)_2$), zinc sulfate ($ZnSO_4$), etc., may be used, and in addition to the above-described zinc salts, all of any zinc precursor that has been used for manufacturing the zinc dicarboxylate-based catalyst may be used without particular limitation.

In addition, since examples of the dicarboxylic acid and examples of the monocarboxylic acid are previously described, additional description thereof will be omitted.

Further, in the manufacturing method of the catalyst, the reaction step of the dicarboxylic acid may be performed at a temperature of about 40 to 90° C. for about 0.5 to 10 hours, and the reaction step of the monocarboxylic acid may be performed at a temperature of about 80 to 150° C. for about 1 to 20 hours.

Accordingly, agglomeration among the catalyst particles in the manufacturing process of the catalyst may be effectively suppressed while securing appropriate production of the zinc dicarboxylate-based catalyst, such that the catalyst having a more uniform and finer particle size and showing an excellent activity may be appropriately manufactured.

Further, in the manufacturing process of the catalyst, the monocarboxylic acid may be used at about 0.1 to 0.5 molar ratio relative to 1 mol of the dicarboxylic acid, and the dicarboxylic acid may be used at about 1.0 to 1.5 molar ratio relative to 1 mol of the zinc precursor.

Accordingly, agglomeration among the catalyst particles in the manufacturing process of the catalyst may be more effectively suppressed while securing appropriate production of the zinc dicarboxylate-based catalyst having an excellent activity, such that the catalyst having a more uniform and finer particle size and showing an excellent activity may be appropriately manufactured.

Meanwhile, according to still another exemplary embodiment of the present invention, there is provided a manufacturing method of a polyalkylene carbonate resin including: polymerizing epoxide and a monomer including carbon dioxide in the presence of the above-described organic zinc catalyst.

In the manufacturing method of the catalyst, the organic zinc catalyst may be used as a non-uniform catalyst form, and the polymerization step may be performed in an organic solvent by solution polymerization.

Accordingly, a heat of reaction may be appropriately controlled, and a molecular weight or a viscosity of the polyalkylene carbonate resin to be preferably obtained may be easily controlled.

In the solution polymerization, as the solvent, at least one selected from the group consisting of methylene chloride, ethylene dichloride, trichloroethane, tetrachloroethane, chloroform, acetonitrile, propionitrile, dimethylformamide, N-methyl-2-pyrrolidone, dimethyl sulfoxide, nitromethane, 1,4-dioxane, hexane, toluene, tetrahydrofuran, methyl ethyl ketone, methyl amine ketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene, and methyl propasol may be used.

Among these examples of the solvent, when methylene chloride or ethylene dichloride is used as the solvent, the polymerization reaction may be more effectively performed.

The solvent may be used at a weight ratio of about 1:0.5 to 1:100, preferably, at a weight ratio of about 1:1 to 1:10 relative to the epoxide.

Here, when the ratio is less than about 1:0.5, which is excessively small, the solvent does not appropriately function as a reaction medium, such that it may be difficult to obtain the above-described advantages of the solution polymerization.

Further, when the ratio is more than about 1:100, the concentration of epoxide, etc., is relatively decreased, such that productivity may be deteriorated, and a molecular weight of a finally formed resin may be decreased, or a side reaction may be increased.

Further, the organic zinc catalyst may be added at a molar ratio of about 1:50 to 1:1000 relative to the epoxide.

More preferably, the organic zinc catalyst may be added at a molar ratio of about 1:70 to 1:600, or about 1:80 to 1:300 relative to the epoxide.

When the molar ratio is excessively small, it is difficult to show a sufficient catalytic activity at the time of the solution polymerization. On the contrary, when the molar ratio is excessively large, since an excessive amount of the catalyst is used, the reaction is not efficiently performed, by-products may occur, or back-biting of the resin by heating in the presence of the catalyst may occur.

Meanwhile, as the epoxide, at least one selected from the group consisting of C2-C20 alkylene oxide unsubstituted or substituted with halogen or C1-C5 alkyl group; C4-C20 cycloalkylene oxide unsubstituted or substituted with halogen or C1-C5 alkyl group; and C8-C20 styrene oxide unsubstituted or substituted with halogen or C1-C5 alkyl group may be used.

Representatively, as the epoxide, C2-C20 alkylene oxide unsubstituted or substituted with halogen or C1-C5 alkyl group may be used.

Specific examples of the epoxide include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrine, epichlorohydrine, epibromohydrine, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxy norbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, and the like.

As the most representative example, ethylene oxide is used as the epoxide.

In addition, the above-described solution polymerization may be performed at about 50 to 100° C. and about 15 to 50 bar for about 1 to 60 hours.

Further, it is more preferable to perform the solution polymerization at about 70 to 90° C. and about 20 to 40 bar for about 3 to 40 hours.

Meanwhile, since the remaining polymerization process and condition except for the above description may follow general polymerization condition, etc., for manufacturing the polyalkylene carbonate resin, additional descriptions thereof will be omitted.

According to the present invention, the present invention may provide an organic zinc catalyst for manufacturing the polyalkylene carbonate resin, capable of effectively suppressing agglomeration among catalyst particles during a manufacturing process of the catalyst, to thereby have a finer and more uniform particle size, and show an excellent activity, and a manufacturing method thereof.

BRIEF DESCRIPTION OF THE DRAWINGS

FIGS. 1 and 2 are scanning electron microscope (SEM) images of organic zinc catalysts obtained from Example 1 and Comparative Example 1, respectively.

DETAILED DESCRIPTION OF THE EMBODIMENTS

Hereinafter, preferable Examples of the present invention will be provided for better understanding of the present invention.

However, the following Examples are provided only for illustration of the present invention, and should not be construed as limiting the present invention by the examples.

EXAMPLE 1

Manufacture of Organic Zinc Catalyst 6.6 g (0.05 mol) of a glutaric acid and 0.1 mL of acetic acid were added to 100 mL toluene in a 250 mL size round bottom flask, and dispersed under reflux.

Then, the mixture was heated at a temperature of 55° C. for 30 minutes, and 4.1 g (0.05 mol) of ZnO was added to 50 mL of toluene, and dispersed. The obtained product was added to the glutaric acid dispersion, and stirred for 3 hours.

Next, 0.02 mol of valeric acid was slowly added thereto with a pipette, and heated at 110° C. for 4 hours.

A white solid was produced, filtered and washed with acetone/ethanol, and dried in a vacuum oven at 130° C.

According to the above-described method, the organic zinc catalyst of Example 1 was manufactured, and then, a chemical structure thereof was confirmed.

In addition, a scanning electron microscope (SEM) image of the organic zinc catalyst of Example 1 was shown in FIG. 1.

It was confirmed from the SEM analysis that the organic zinc catalyst of Example 1 had an average particle size of about 0.52 µm and a particle size standard deviation of about 0.27 µm.

EXAMPLE 2

Manufacture of Organic Zinc Catalyst

An organic zinc catalyst of Example 2 was manufactured in the same manner as Example 1 except for using a lauric acid instead of using the valeric acid in Example 1, and a chemical structure thereof was confirmed.

Further, the organic zinc catalyst of Example 2 was confirmed by SEM analysis. As a result, it was confirmed that the organic zinc catalyst of Example 2 had an average particle size of about 0.48 µm and a particle size standard deviation of about 0.28 µm.

EXAMPLE 3

Manufacture of Organic Zinc Catalyst

An organic zinc catalyst of Example 3 was manufactured in the same manner as Example 1 except for using an acetoacetic acid instead of using the valeric acid in Example 1, and a chemical structure thereof was confirmed.

Further, the organic zinc catalyst of Example 3 was confirmed by SEM analysis. As a result, it was confirmed that the organic zinc catalyst of Example 3 had an average particle size of about 0.57 µm and a particle size standard deviation of about 0.23 µm.

EXAMPLE 4

Manufacture of Organic Zinc Catalyst

An organic zinc catalyst of Example 4 was manufactured in the same manner as Example 1 except for using 5-hydroxy-4-oxo-4H-pyran-2-carboxylic acid instead of using the valeric acid in Example 1, and a chemical structure thereof was confirmed.

Further, the organic zinc catalyst of Example 4 was confirmed by SEM analysis. As a result, it was confirmed that the organic zinc catalyst of Example 4 had an average particle size of about 0.51 µm and a particle size standard deviation of about 0.28 µm.

COMPARATIVE EXAMPLE 1

Manufacture of Organic Zinc Catalyst

An organic zinc catalyst of Comparative Example 1 was manufactured in the same manner as Example 1 except for not using the valeric acid in Example 1, and a chemical structure thereof was confirmed.

In addition, a scanning electron microscope (SEM) image of the organic zinc catalyst of Comparative Example 1 was shown in FIG. 2.

COMPARATIVE EXAMPLE 2

Manufacture of Organic Zinc Catalyst

An organic zinc catalyst of Comparative Example 2 was manufactured in the same manner as Example 1 except for using a propionic acid instead of using the valeric acid in Example 1, and a chemical structure thereof was confirmed.

Further, the organic zinc catalyst of Comparative Example 2 was confirmed by SEM analysis. As a result, it was confirmed that the organic zinc catalyst of Comparative Example 2 had an average particle size of about 0.73 µm and a particle size standard deviation of about 0.34 µm.

Referring to FIGS. 1 and 2 and the above-described respective Examples and Comparative Examples, it was confirmed that the organic zinc catalysts manufactured by using the monocarboxylic acid having a C3-C15 aliphatic hydrocarbon group in Examples 1 to 4 had more uniform and finer particle size as compared to the organic zinc catalyst of Comparative Example 1 manufactured without using the monocarboxylic acid or the organic zinc catalyst of Comparative Example 2 manufactured by using the monocarboxylic acid to which less than 3 hydrocarbon groups is bonded, i.e., propionic acid.

POLYMERIZATION EXAMPLE

Polyethylene carbonates were polymerized and manufactured by performing the following method and using the catalysts of Examples 1 to 4 and Comparative Examples 1 and 2.

First, 0.4 g of each catalyst and 8.52 g of dichloromethane were added to a high-pressure reactor in a glove box, and 8.9 g of ethylene oxide was added.

Then, the mixture was pressed in the reactor by a pressure of 30 bar using carbon dioxide.

The polymerization reaction was performed at 70° C. for 3 hours.

After the reaction was completed, unreacted carbon dioxide and ethylene oxide were removed together with dichloromethane which is a solvent.

In order to measure an amount of the manufactured polyethylene carbonate, the remaining solid was completely dried and quantified.

Each activity and yield of the catalysts according to the polymerization results were shown in Table 1 below.

TABLE 1

| | Kinds of Monocarboxylic acid | Yield (g) | Activity of catalyst (g-polymer/g-catalyst) |
|---|---|---|---|
| Example 1 | Valeric acid | 15.2 | 38.0 |
| Example 2 | Lauric acid | 13.9 | 34.8 |
| Example 3 | Acetoacetic acid | 14.1 | 35.25 |
| Example 4 | 5-hydroxy-4-oxo-4H-pyran-2-carboxylic acid | 14.6 | 36.5 |
| Comparative Example 1 | None | 13.2 | 33.0 |
| Comparative Example 2 | Propionic acid | 10.8 | 27.0 |

Referring to Table 1 above, it was confirmed that the catalysts of Examples 1 to 4 had more excellent activity than those of Comparative Examples 1 and 2. In addition, from the catalysts of Examples 1 to 4, the polyethylene carbonate could be manufactured at an excellent yield.

What is claimed is:

1. An organic zinc catalyst which is a zinc dicarboxylate-based organic zinc catalyst used for a reaction in which a polyalkylene carbonate resin is manufactured from carbon dioxide and epoxide, the organic zinc catalyst comprising:
    a moiety having a C4-C15 aliphatic hydrocarbon group (R) bonded to an end of at least one side of the zinc dicarboxylate-based organic zinc catalyst,
    wherein the moiety having a C4-C15 aliphatic hydrocarbon group (R) is derived from a monocarboxylic acid (R—COOH),
    wherein the moiety having a C4-C15 aliphatic hydrocarbon group (R) optionally inlcudes at least one oxygen or carbonyl group,
    wherein the organic zinc catalyst has a particle shape having an average particle size of 0.2 to 0.9 µm and a particle size standard deviation of 0.05 to 0.3 µm, and
    wherein the monocarboxylic acid-derived moiety is bonded at 0.2 to 0.5 molar ratio relative to 1 mol of a dicarboxylate-derived moiety of the organic zinc catalyst.

2. The organic zinc catalyst of claim 1, wherein: the zinc dicarboxylate-based organic zinc catalyst is a catalyst in which zinc is bonded to C3-C20 aliphatic dicarboxylate or C8-C40 aromatic dicarboxylate.

3. The organic zinc catalyst of claim 1, wherein: the zinc dicarboxylate-based organic zinc catalyst is a zinc glutarate-based catalyst.

4. The organic zinc catalyst of claim 1, wherein: the monocarboxylic acid includes at least one selected from the group consisting of valeric acid, lauric acid, 3,5-dioxo-hexanoic acid, 3,5,7-trioxo-dodecanoic acid, acetoacetic acid, levulinic acid, 4-oxo-4H-1-benzopyran-2-carboxylic acid, and 5-hydroxy-4-oxo-4H-pyran-2-carboxylic acid.

5. A manufacturing method of the organic zinc catalyst of claim 1 comprising:
    reacting a zinc precursor, a dicarboxylic acid, and a monocarboxylic acid having a C4-C15 aliphatic hydrocarbon group with or without at least one oxygen or carbonyl group,
    wherein the monocarboxylic acid-derived moiety is bonded at 0.2 to 0.5 molar ratio relative to 1 mol of a dicarboxylate-derived moiety of the organic zinc catalyst.

6. The manufacturing method of claim 5, wherein:
    the reaction step includes reacting the zinc precursor with the dicarboxylic acid, and
    further reacting with the monocarboxylic acid.

7. The manufacturing method of claim 5, wherein:
    the zinc precursor includes a compound selected from the group consisting of zinc oxide, zinc hydroxide, zinc acetate ($Zn(O_2CCH_3)_2$), zinc nitrate ($Zn(NO_3)_2$) and zinc sulfate ($ZnSO_4$).

8. The manufacturing method of claim 6, wherein:
    the reaction step with the dicarboxylic acid is performed at a temperature of 40 to 90° C. for 0.5 to 10 hours, and the reaction step of the monocarboxylic acid is performed at a temperature of 80 to 150° C. for 1 to 20 hours.

9. The manufacturing method of claim 5, wherein:
    the monocarboxylic acid is used at 0.1 to 0.5 molar ratio relative to 1 mol of the dicarboxylic acid.

10. The manufacturing method of claim 5, wherein:
    the dicarboxylic acid is used at 1.0 to 1.5 molar ratio relative to 1 mol of the zinc precursor.

11. A manufacturing method of a polyalkylene carbonate resin comprising:

polymerizing epoxide and a monomer including carbon dioxide in the presence of the organic zinc catalyst of claim 1.

12. The manufacturing method of claim 11, wherein:
the manufacturing method is performed in an organic solvent by solution polymerization.

\* \* \* \* \*